United States Patent
Kokubo et al.

(10) Patent No.: US 7,871,561 B2
(45) Date of Patent: Jan. 18, 2011

(54) ARTIFICIAL BONE AND METHOD FOR PRODUCING THE SAME

(75) Inventors: Tadashi Kokubo, Nagaokakyo (JP); Takehiro Shibuya, Otsu (JP)

(73) Assignee: Japan Science and Technology Agency, Saitama (JP)

( * ) Notice: Subject to any disclaimer, the term of this patent is extended or adjusted under 35 U.S.C. 154(b) by 589 days.

(21) Appl. No.: 11/887,398

(22) PCT Filed: Mar. 22, 2006

(86) PCT No.: PCT/JP2006/305664

§ 371 (c)(1),
(2), (4) Date: Sep. 28, 2007

(87) PCT Pub. No.: WO2006/109461

PCT Pub. Date: Oct. 19, 2006

(65) Prior Publication Data

US 2009/0270998 A1    Oct. 29, 2009

(30) Foreign Application Priority Data

Mar. 31, 2005 (JP) ............... 2005-101104

(51) Int. Cl.
*B22F 3/11* (2006.01)
*A61F 2/28* (2006.01)

(52) U.S. Cl. ............ 419/2; 428/307.3; 623/23.55; 419/23; 419/34

(58) Field of Classification Search ............... None
See application file for complete search history.

(56) References Cited

U.S. PATENT DOCUMENTS

2006/0122708 A1    6/2006    Nakamura et al.

OTHER PUBLICATIONS

Asahina, T. et al., "Method for Manufacturing High-Strength Porous Body," Patent Abstracts of Japan, JP. No. 2002-285203, Published on Oct. 3, 2002.
Fujibayashi, S. et al., "Osteoinduction of Porous Bioactive Titanium Metal," Biomaterials, vol. 25, pp. 443-450, (2004).
Wen, C. E. et al., "Novel Titanium Foam for Bone Tissue Engineering," J. Mater. Res., vol. 17, No. 10, pp. 2633-2639, (Oct. 2002).
Asahina, T. et al., "Porous Body for Impact Absorption, and its Manufacturing Method," Patent Abstracts of Japan, JP. No. 2003-171704, Published on Jun. 20, 2003.

(Continued)

*Primary Examiner*—Ling Xu
(74) *Attorney, Agent, or Firm*—Finnegan, Henderson, Farabow, Garrett & Dunner, L.L.P.

(57) ABSTRACT

An artificial bone which is excellent in the ability to form bone in a living body, reliably thereof, and has high mechanical strength. The process comprises the steps of: mixing granules, composed of a titanium or a titanium alloy powder and an organic binder, with a particulate pore-forming material, pressure-molding the mixture to obtain a molded body, firing the molded body at 1200° C. to obtain a porous body, bringing the porous body into contact with an aqueous alkali solution, subsequently with water of 35° C. or higher for a period longer than that of contacting with the aqueous alkali solution and then heating the porous body at 100 to 650° C., preferably 200 to 600° C.

4 Claims, 2 Drawing Sheets

OTHER PUBLICATIONS

Matsuno, N. et al., "Production of Porous Body Having Excellent Osteoaffinity," Patent Abstracts of Japan, JP. No. 03-049766, Published on Mar. 4, 1991.

Kumagai, M. et al., "Titanium Aluminide Material Having Excellent Bioadaptability," Patent Abstracts of Japan, JP. No. 05-269195, Published on Oct. 19, 1993.

Kawatani, Y. et al., "Implant Member," Patent Abstracts of Japan, JP. No. 06-154257, Published on Jun. 3, 1994.

Kokubo, T. et al., "Titanium Oxide/Organic Polymer Composite Suitable as Artificial Bone and The Like," Patent Abstracts of Japan, JP. No. 2002-327079, Published on Nov. 15, 2002.

ARTIFICIAL BONE AND METHOD FOR PRODUCING THE SAME

TECHNICAL FIELD

The present invention relates to an artificial bone and a method for producing the same. Artificial bone produced by the method according to the present invention has high biocompatibility and excellent ability to form bone, and is therefore suitable for use as a bone substitute material.

BACKGROUND ART

Titanium is highly chemically durable in a living body and is highly biocompatible, and is therefore expected to be used as a bone substitute material. A bone substitute material to be implanted in a living body is desired to be porous because of the necessity to form bone or bond to surrounding bone in it. A titanium porous body is generally obtained by pressure-molding a titanium powder, which is mixed with a pore-forming material if necessary, to obtain a molded body and then sintering the molded body (see Patent Document 1). It is conventionally known that by bringing such a titanium porous body into contact with an aqueous alkali solution, it is possible to allow the surface of the titanium porous body to have the ability to form apatite (see Non-Patent Documents 1 and 2). Further, it is disclosed that artificial bone produced by forming a titanium porous body by plasma spraying, alkali-treating the titanium porous body in the same manner as described above, and immersing the alkali-treated titanium porous body in hot water has the ability to form bone in a living body even when it is implanted in an area where living bone does not exist (see Patent Document 2).

Patent Document 1: Japanese Patent Application Laid-open No. 2002-285203

Patent Document 2: WO 2004/062705A1

Non-Patent Document 1: J. Mater. Res., Vol. 17, No. 10, October 2002

Non-Patent Document 2: Biomaterials 25 (2004) 443-450

DISCLOSURE OF THE INVENTION

Problems to be Solved by the Invention

However, when a large compression force is applied to the aforementioned conventional artificial bone so that the artificial bone is deformed, there is a case where some titanium particles are peeled off from the artificial bone. In this case, if the particles that have peeled off the artificial bone are dispersed in a living body, the living body regards the particles as foreign matters and rejects them even when the artificial bone is made of a material having excellent biocompatibility. However, it is difficult for them to be completely removed from the living body.

It is therefore an object of the present invention to provide artificial bone having the ability to form bone in a living body, excellent reliably thereof, and high mechanical strength.

Means for Solving the Problems

In order to solve the problems, a method for producing artificial bone of the present invention is characterized in including the steps of: obtaining a porous body having a porosity and an average pore size lying within a range enclosed with lines connecting the X (porosity (%)) and Y (average pore size (μm)) coordinates of points A (46, 180), B (46, 520), C (50, 520), D (72, 220), and E (72, 180) shown in FIG. 1 by mixing granules, composed of a titanium or a titanium alloy powder and an organic binder, with a particulate pore-forming material, pressure-molding the mixture to obtain a molded body, and firing the molded body; then bringing the porous body into contact with an aqueous alkali solution; bringing the porous body into contact with water until the alkali concentration of the porous body becomes 0.3 at % or less; and subsequently heating the porous body at 60° C. or higher but 650° C. or lower.

According to the production method of the present invention, metal powder and an organic binder are previously mixed to obtain granules. More specifically, a molded body is obtained by compressing a mixture of a pore-forming material and a large number of granules composed of clusters of primary metal particles having a maximum particle size of 180 μm or less and an organic binder. That is, as shown in FIG. 2, granules 1 contains a large number of primary particles 2 contacted not only with each other but also with primary particles of the neighboring granules, and a large pore-forming material 3 is present among the granules. Therefore, when such a molded body is fired, the pore-forming material is removed to provide pores communicating with one another, and not only the primary particles 2 in each granule 1 but also a large number of primary particles 2 contacted with the adjacent granules 1 are bonded together. As a result, it is possible to obtain a sintered body having high mechanical strength in spite of its high porosity. In addition, even when a compressive load is imposed on the sintered body, particles are not peeled off the sintered body. Further, since the pores in the sintered body communicate with one another, an aqueous solution can easily pass through the sintered body.

Therefore, surfaces of pores in the interior are corroded by the aqueous alkali solution to thereby become active and have large roughness. Then, by substantially completely removing the alkali ions from the porous body, the surface is allowed to have an amorphous titanium oxide phase or an anatase phase having low crystallinity. Then, by heating the porous body at 60° C. or higher but 650° C. or lower, the surface is modified to have an anatase phase having high crystallinity and excellent ability to form bone. If the heating temperature is less than 60° C., modification of the surface is not sufficiently performed. On the other hand, if the heating temperature exceeds 650° C., a large amount of a rutile phase whose ability to form bone is inferior to that of an anatase phase is formed. In order to substantially completely remove the alkali component from the porous body, it is desired that the porous body is brought into contact with water having a temperature of 35° C. or higher for a longer time than that for bringing the porous body into contact with the aqueous alkali solution, and also during this time, the water is changed to fresh one at least once. The heating of the porous body for modification to provide an anatase phase may be performed in the prior step of the heating step, that is, in the step of bringing the porous body into contact with water. More specifically, removal of the alkali component and modification to provide an anatase phase can be performed at the same time by setting the temperature of water to be brought into contact with the porous body to remove the alkali component to 60° C. or higher.

The artificial bone produced by the method according to the present invention is characterized in including: a porous body made of titanium or a titanium alloy and having a porosity and an average pore size lying within a range enclosed with lines connecting the X (porosity (%)) and Y (average pore size (μm)) coordinates of points A (46, 180), B (46, 520), C (50, 520), D (72, 220), and E (72, 180); and a layer composed of anatase phase formed on the inner surface of pores of the porous body.

EFFECT OF THE INVENTION

According to the present invention, it is possible to obtain artificial bone having the ability to form bone in a living body, excellent reliability thereof, and high mechanical strength.

DESCRIPTION OF SYMBOLS

Figure 1:
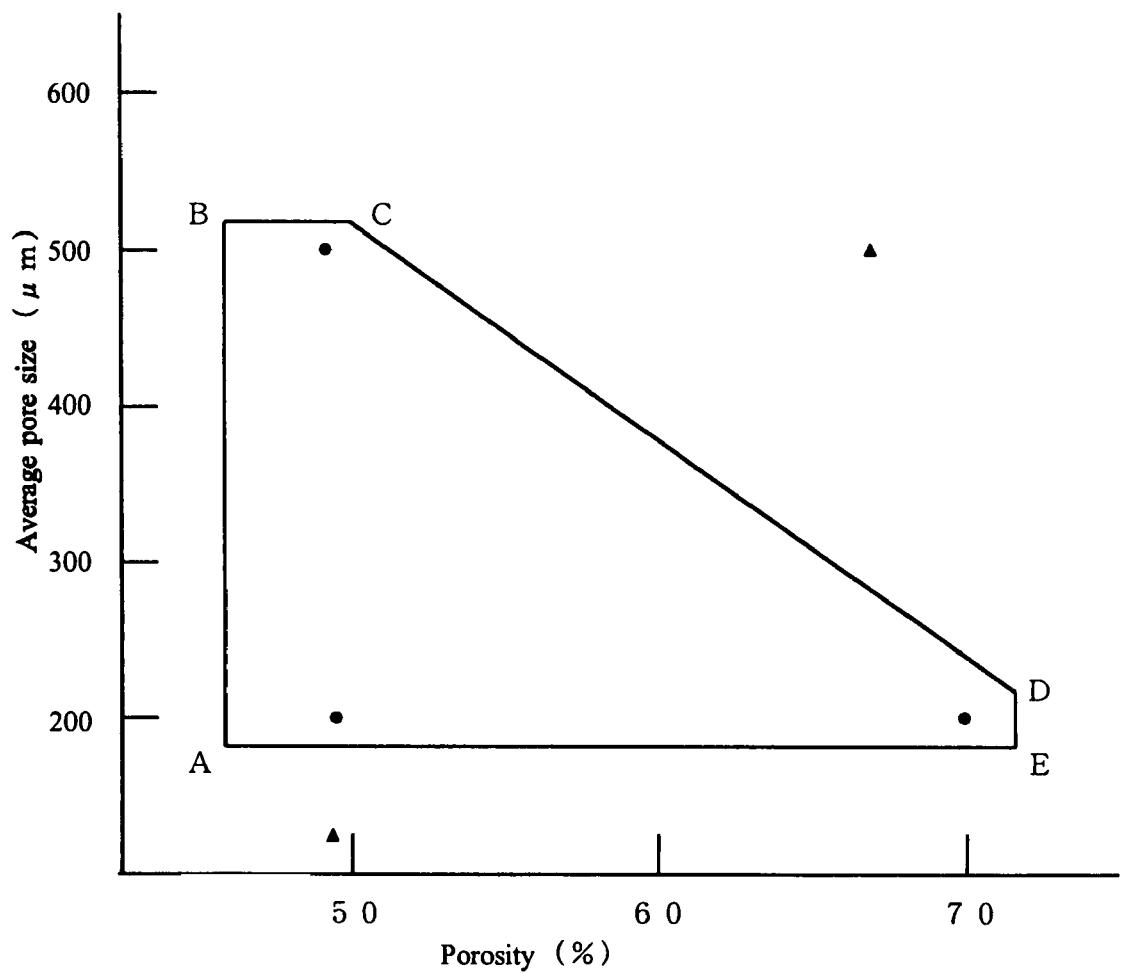
FIG. 1 is a graph which shows the relationship between a porosity and an average pore size of a porous body used in the present invention, wherein the symbol "●" (solid circle) represents an example, and the symbol "▲" (solid triangle) represents a comparative example.
Figure 2:
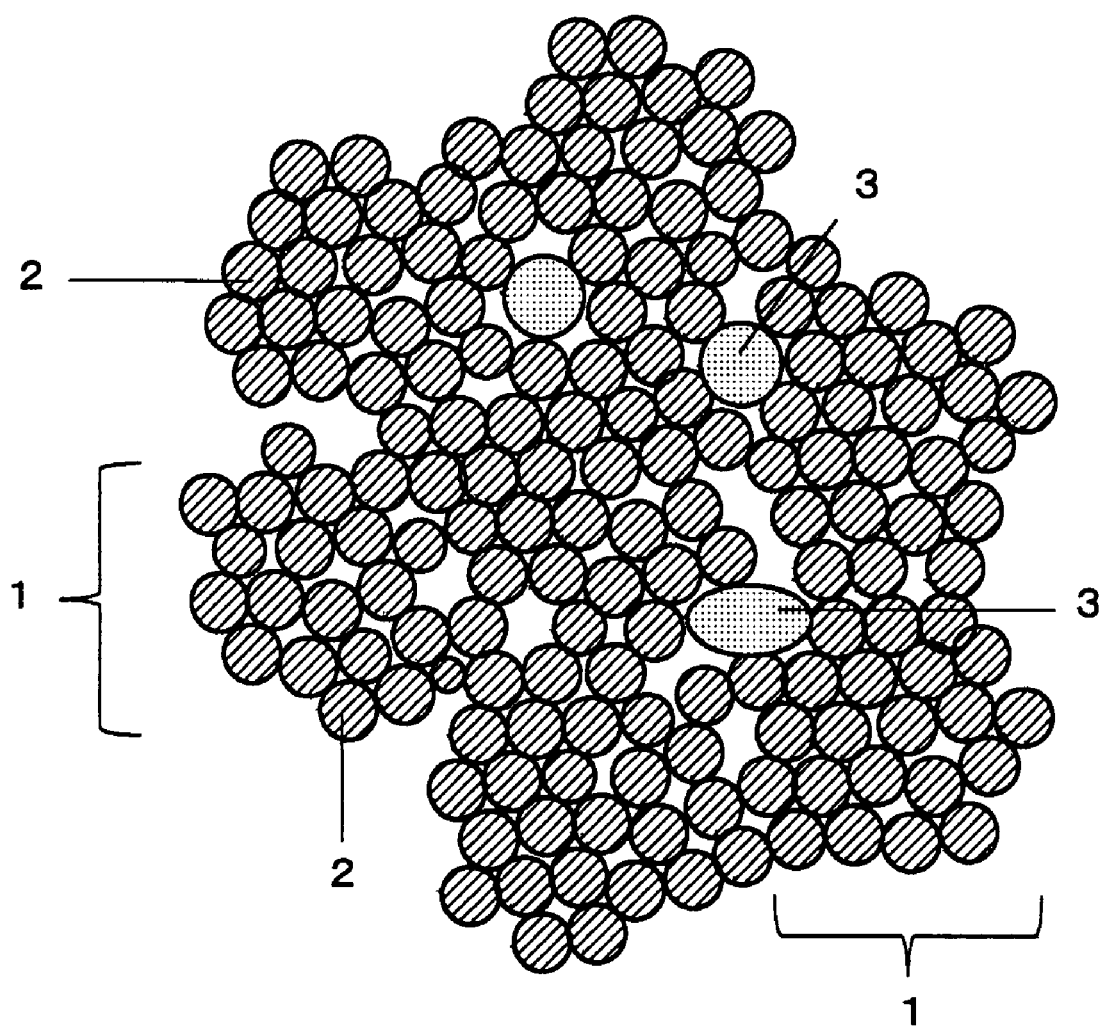
FIG. 2 is an illustration for explaining the effect of the present invention.

1 Granules
2 Primary particles
3 Pore-forming material

BEST MODE FOR CARRYING OUT THE INVENTION

A porous body is preferably formed by mixing granules which are composed of a titanium or a titanium alloy powder having a maximum particle size of 180 μm or less and an organic binder having a granule size in the range of 0.1 to 2.0 mm with a pore-forming material, pressure-molding the mixture to obtain a molded body, and then firing the molded body.

The titanium or titanium alloy powder preferably has an oxygen content of 0.30 wt % or less. Such a powder is active because the amount of oxygen present in the surface of the particles is small, and therefore bonding of primary particles easily proceeds in the firing step. Accordingly, this makes it possible to obtain a porous body having higher mechanical strength.

The organic binder is not particularly limited, and examples thereof include polyacetal, polypropylene, and polyethylene. A metal powder having an oxygen content of 0.30 wt % or less can be obtained by pulverizing a metal in an inert gas atmosphere or by a so-called gas atomization method in which a molten metal is sprayed. Examples of the pore-forming material include compounds which are solid at room temperature but are sublimed or decomposed at 200° C. or less (e.g., ammonium hydrogen carbonate, oxalic anhydride, oxalic acid dihydrate) and mixtures of any one of these compounds with a wax. Such a pore-forming material does not remain in the porous body after it is sublimed or decomposed.

EXAMPLES

In the following description, the term "osteoconductive potential" refers to a phenomenon in which living bone grows into pores of artificial bone implanted in a region where living bone has been present and then bonds to the artificial bone, and the term "osteoinductive potential" refers to a phenomenon in which living bone is formed in pores of artificial bone implanted in muscle.

Example 1

A titanium powder produced by gas atomization so as to have an oxygen content of 0.12 wt % and a maximum particle size of 45 μm and polyacetal (manufactured by Polyplastics Co., Ltd. under the trade name of DURACON M270) were mixed in a volume ratio of 65:35 and kneaded. It is to be noted that the volume ratio was calculated from the true densities and weights of them. The kneaded mixture block was pulverized and passed through a sieve to obtain granules having a granule size in the range of 0.6 to 1.5 mm. Separately, a pore-forming material was prepared by mixing 88 vol % of an ammonium hydrogen carbonate powder with 12 vol % of a paraffin wax, and then the particle size of the pore-forming material was adjusted to 250 to 500 μm.

Then, the granules and the pore-forming material were mixed in a volume ratio of 65:35. The thus obtained mixed powder was charged into a mold, and was then heated to 130° C. and pressed at 80 MPa to obtain a molded body. The molded body was placed in a vacuum furnace, degreased, and maintained at 1200° C. for 2 hours to obtain a columnar titanium porous body having a diameter of 22 mm and a height of 18 mm. The porosity of the porous body was measured by a mercury porosimeter (manufactured by Micromeritics Instrument Corporation) and was found to be 49%. A specimen having a diameter of 6 mm and a height of 10 mm was cut out from the porous body, and was then compressed at a compression rate of 1 mm/min. As a result, the specimen was deformed without peeling off fragments and the compressive strength of the porous body was found to be 116 MPa. Further, a CT cross section of the specimen was observed, and as a result the average pore size of the porous body was found to be 200 μm.

Then, another specimen having a diameter of 6 mm and a height of 15 mm was cut out from the porous body, and was then immersed in a 5M aqueous sodium hydroxide solution having a temperature of 60° C. for 24 hours, and subsequently in distilled water having a temperature of 40° C. for 48 hours (the distilled water was changed to fresh one every 12 hours, and the same goes for the following examples), and was then heated at 600° C. for 1 hour (hereinafter, referred to as "alkali-hot water-heat treatments"). A titanium plate having a purity of 99% was also subjected to the alkali-hot water-heating treatment in the same manner as described above. The specimen was analyzed using an energy dispersive X-ray analyzer (EDX) under conditions where an accelerating voltage was 15 kV, elements to be measured were O, Na, and Ti, an X-ray intensity was in the range of 1,500 to 2,500 cps, and count accumulation time was 1000 sec. As a result, Na ions were not detected at any depths of 0, 1, 2, and 3 mm from the surface of the specimen. Further, the crystalline phase of the titanium plate was analyzed using an X-ray diffraction device, and as a result, it was found that a large amount of anatase and a small amount of rutile had been deposited on the titanium plate.

The specimen was implanted in a tibial bone of an adult white rabbit and was left for 8 weeks. As a result, the porous body directly bonded to the tibial bone. The specimen was taken out of the rabbit together with the surrounding bone, and was then cut along its radial direction. The cross section of the specimen was observed using a scanning electron microscope, and as a result, it was found that living bone had actively and uniformly grown into the specimen in a direction from the surface to the center of the specimen and had bonded to the specimen. This indicates that the porous body of Example 1 has excellent osteoconductive potential.

Further, another specimen cut out from the porous body and subjected to the alkali-hot water-heat treatments in the same manner as described above was implanted in a dorsal muscle of an adult beagle dog, and was then taken out of the dog after 3 months. The specimen was cut along its radial direction, and the cross section of the specimen was observed using a scanning electron microscope. As a result, it was found that bone had been almost uniformly formed on the entire surface of pores inside the specimen. This indicates that the porous body of Example 1 has excellent osteoinductive potential.

Comparative Example 1

A titanium powder produced by gas atomization so as to have an oxygen content of 0.12 wt % and a maximum particle size of 45 μm and polyacetal (same as above) were mixed in a volume ratio of 65:35 and kneaded. It is to be noted that the volume ratio was calculated from the respective true densities and weights. The kneaded mixture block was pulverized and passed through a sieve to obtain granules having a granule size in the range of 0.6 to 1.5 mm. The granules were charged into a mold, and were then heated to 130° C. and pressed by a press machine whose stroke was adjusted so that the volume of the granules in the mold was reduced to 64% when the initial volume of the granules in the mold was defined as 100%, to thereby obtain a molded body. The molded body was placed in a vacuum furnace, degreased, and maintained at 1200° C. for 2 hours to obtain a columnar titanium porous body having a diameter of 22 mm and a height of 18 mm.

The porosity of the porous body was measured using a mercury porosimeter and was found to be 49%. The oxygen content of the porous body was analyzed by an infrared diffuse refrectance method and was found to be 0.21 wt %. The compressive strength of the porous body was 116 MPa, and in this measurement, the porous body was deformed without peeling off fragments. The average pore size of the porous body was 150 μm.

A specimen was cut out from the porous body, and was then subjected to the alkali-hot water (provided that distilled water was not changed)—heating treatment, and was then analyzed by EDX in the same manner as in Example 1. As a result, Na ions were locally detected at a concentration of 0.4 to 1.2 at % irrespective of a distance from the surface of the specimen. Further, the osteoconductive potential and osteoinductive potential of the porous body were checked in the same manner as in Example 1. In the test of osteoconductive potential, the outer peripheral surface of the specimen was entirely covered with bone newly formed, but some pores present near the center of the specimen did not contain bone. In the test of the osteoinductive potential, an area where bone was not formed was locally present in the specimen.

Example 2

A titanium porous body was formed in the same manner as in Example 1 except that the titanium powder was changed to one having a maximum particle size of 180 μm and the ammonium hydrogen carbonate powder was changed to one whose particle size was adjusted to 500 to 1500 μm. The porosity of the porous body was measured using a mercury porosimeter and was found to be 48%. The compressive strength of the porous body was 118 MPa, and in this measurement, the porous body was deformed without peeling off fragments. The average pore size of the porous body was 500 μm.

A specimen was cut out from the porous body, and was then subjected to the alkali-hot water-heating treatment to check the osteoconductive potential and osteoinductive potential of the porous body in the same manner as in Example 1. As a result, the porous body of Example 2 had excellent osteoconductive potential and osteoinductive potential as in the case of the porous body of Example 1. Na ions were not detected in the porous body of Example 2.

Comparative Example 2

A titanium powder produced by gas atomization so as to have an oxygen content of 0.12 wt % and a maximum particle size of 180 μm and polyacetal (same as above) were mixed in a volume ratio of 70:30 and kneaded. The kneaded mixture block was pulverized and passed through a sieve to obtain granules having a granule size in the range of 0.6 to 1.5 mm. Separately, the particle size of an ammonium hydrogen carbonate powder was adjusted to 500 to 1500 μm. The granules and the ammonium hydrogen carbonate powder were mixed in a volume ratio of 58:42, and the mixture was charged into a mold, and was then heated to 130° C. and pressed at 80 MPa to obtain a molded body. The molded body was placed in a vacuum furnace, degreased, and maintained at 1250° C. for 2 hours to obtain a columnar titanium porous body having a diameter of 22 mm and a height of 20 mm.

The porosity of the porous body was measured using a mercury porosimeter and was found to be 67%. The compressive strength of the porous body was 32 MPa, and in this measurement, the porous body was deformed without peeling off fragments. The average pore size of the porous body was 500 μm. A specimen was cut out from the porous body, and was then subjected to the alkali-hot water-heat treatments to check the osteoconductive potential and the osteoinductive potential of the porous body in the same manner as in Example 1. As a result, the porous body of Comparative Example 2 had excellent osteoconductive potential as in the case of the porous body of Example 1, but the osteoinductive potential was poor. Na ions were not detected in the porous body of Comparative Example 2.

Comparative Example 3

A specimen was cut out from the titanium porous body obtained in Example 1, and then the osteoconductive potential and osteoinductive potential of the specimen were checked without carrying out the alkali-hot water-heat treatments. In the test of the osteoconductive potential, the amount of living bone that had grown into the specimen was small, and bonding between living bone and the specimen was not observed. In addition, the osteoinductive potential was not observed at all.

Comparative Example 4

A specimen was cut out from the titanium porous body obtained in Comparative Example 2, and then the osteoconductive potential and the osteoinductive potential of the specimen were checked without carrying out the alkali-hot water-heating treatment. As for the osteoconductive potential, the amount of living bone that had grown into the specimen was small, and bonding between living bone and the specimen was not observed. In addition, the osteoinductive potential was not observed at all.

Example 3

A titanium alloy (Ti-6Al-4V) powder produced by gas atomization so as to have an oxygen content of 0.18 wt % and a maximum particle size of 180 μm and polyacetal (same as above) were mixed in a volume ratio of 65:35 and kneaded. The kneaded mixture block was pulverized and passed through a sieve to obtain granules having a granule size in the range of 0.6 to 1.5 mm. Separately, the particle size of an ammonium hydrogen carbonate powder was adjusted to 500 to 1500 μm. The granules and the ammonium hydrogen carbonate powder were mixed in a volume ratio of 65:35, and the mixture was charged into a mold, and was then heated to 130° C. and pressed at 80 MPa to obtain a molded body. The molded body was placed in a vacuum furnace, degreased, and maintained at 1380° C. for 2 hours to obtain a columnar titanium alloy porous body having a diameter of 22 mm and a height of 18 mm. The porosity of the porous body was measured using a mercury porosimeter and was found to be 48%. The compressive strength of the porous body was 215 MPa, and in this measurement, the porous body was deformed without peeling off fragments. The average pore size of the porous body was 500 μm.

A specimen having a diameter of 6 mm and a height of 15 mm was cut out from the porous body, immersed in a 5M aqueous sodium hydroxide solution having a temperature of 60° C. for 24 hours and subsequently in distilled water having a temperature of 80° C. for 48 hours, and then heated at 500° C. for 1 hour. The osteoconductive potential of the porous body was checked in the same manner as in Example 1, and as a result it was found that the porous body had excellent osteoconductive potential as in the case of the porous body of Example 1. At the same time, a titanium alloy (Ti-6Al-4V) plate was also subjected to the alkali-hot water-heat treatments in the same manner as described above. Then, the crystalline phase of the titanium alloy plate was analyzed using an X-ray diffraction, and as a result, it was found that a large amount of anatase had been deposited on the titanium alloy plate.

Example 4

A titanium alloy (Ti-6Al-4V) powder produced by gas atomization so as to have an oxygen content of 0.21 wt % and a maximum particle size of 45 μm and polyacetal (same as above) were mixed in a volume ratio of 70:30 and kneaded. The kneaded mixture block was pulverized and passed through a sieve to obtain granules having a granule size in the range of 0.3 to 0.65 mm. Separately, a pore-forming material was prepared by mixing 88 vol % of oxalic anhydride with 12 vol % of a paraffin wax, and then the particle size of the pore-forming material was adjusted to 250 to 500 μm.

Then, the thus obtained granules and pore-forming material were mixed in a volume ratio of 58:42, and the mixed powder was charged into a mold, and was then heated to 130° C. and pressed at 80 MPa to obtain a molded body. The molded body was placed in a vacuum furnace, degreased, and maintained at 1250° C. for 2 hours to obtain a columnar titanium alloy porous body having a diameter of 22 mm and a height of 20 mm. The porosity of the porous body was measured using a mercury porosimeter and was found to be 70%. The compressive strength of the porous body was 105 MPa, and in this measurement, the porous body was deformed without peeling off fragments. The average pore size of the porous body was 200 μm.

A specimen having a diameter of 6 mm and a height of 15 mm was cut out from the porous body, immersed in a 5M aqueous sodium hydroxide solution having a temperature of 60° C. for 24 hours and subsequently in distilled water having a temperature of 40° C. for 48 hours, and then heated at 500° C. for 1 hour. The osteoconductive potential of the porous body was checked in the same manner as in Example 1, and as a result the porous body was found to have excellent osteoconductive potential as in the case of the porous body of Example 1.

Comparative Example 5

A specimen was cut out from the titanium alloy porous body obtained in Example 3, and then the osteoconductive potential of the specimen was checked without carrying out the alkali-hot water-heat treatments. As a result, the amount of living bone that had grown into the specimen was small, and bonding between living bone and the specimen was not observed.

Comparative Example 6

A specimen was cut out from the titanium alloy porous body obtained in Example 4, and then the osteoconductive potential of the specimen was checked without carrying out the alkali-hot water-heat treatments. As a result, the amount of living bone that had grown into the specimen was small, and bonding between living bone and the specimen was not observed.

Example 5

A titanium powder produced by gas atomization so as to have an oxygen content of 0.12 wt % and a maximum particle size of 180 μm and polyacetal were mixed in a volume ratio of 65:35 and kneaded. Then, the kneaded mixture block was pulverized and passed through a sieve to obtain granules having a granule size in the range of 0.6 to 1.5 mm. Separately, a pore-forming material was prepared by mixing 88 vol % of an ammonium hydrogen carbonate powder and 12 vol % of a paraffin wax, and the particle size of the pore-forming material was adjusted to 250 to 500 μm.

Then, the thus obtained granules and pore-forming material were mixed in a volume ratio of 58:42, and the mixed powder was charged into a mold, and was then heated to 130° C. and pressed at 80 MPa to obtain a molded body. The molded body was placed in a vacuum furnace, degreased, and maintained at 1200° C. for 2 hours to obtain a titanium porous body. The porosity of the porous body was measured using a mercury porosimeter and was found to be 70%. The average pore size of the porous body was 200 μm. The compressive strength of the porous body was 40 MPa, and in this measurement, the porous body was deformed without peeling off fragments. A specimen was cut out from the porous body and subjected to the alkali-hot water-heat treatments. Then, the osteoconductive potential and the osteoinductive potential of the specimen were checked in the same manner as in Example 1. As a result, both of the osteoconductive potential and the osteoinductive potential in the porous body of Example 5 were excellent as in the case of the porous body of Example 1.

Comparative Example 7

The same titanium powder as used in Example 5 was charged into a mold and pressed at 80 MPa at room temperature to obtain a molded body. The molded body was easily collapsed by holding it by hand.

Comparative Example 8

The same titanium powder as used in Example 5 and a paraffin wax were mixed in a volume ratio of 95:5, and the mixed powder was charged into a mold, heated to 50° C. and pressed at 80 MPa to obtain a molded body. The molded body was placed in a vacuum furnace, decreased, and maintained at 1200° C. for 2 hours to obtain a columnar titanium porous body having a diameter of 23 mm and a height of 19 mm. The porosity of the porous body was about 30%. The compressive strength of the porous body was 105 MPa, and particles partially peeled off from the porous body in process of the deformation of the porous body.

Comparative Example 9

The same titanium powder as used in Example 5 and an ammonium hydrogen carbonate powder were mixed in a volume ratio of 58:42, and the mixed powder was charged into a mold, heated to 130° C. and pressed at 80 MPa to obtain a molded body. The molded body was placed in a vacuum furnace, degreased, and maintained at 1200° C. for 2 hours to obtain a columnar titanium porous body having a diameter of 23 mm and a height of 19 mm. The porosity of the porous body was 78%. The compressive strength of the porous body was 25 MPa, and particles peeled off from the porous body on process of the deformation of the porous body.

Reference Example

A titanium plate having a purity of 99% was immersed in a 5M aqueous sodium hydroxide solution having a temperature of 60° C. for 24 hours and then in distilled water having a temperature of 80° C. for 48 hours (the distilled water was changed to fresh one having a temperature of 80° C. every 12 hours). The crystalline phase of the titanium plate was analyzed using an X-ray diffraction, and as a result it was found that a large amount of anatase had been deposited on the titanium plate.

The invention claimed is:

1. A method for producing artificial bone, comprising the steps of:

obtaining a porous body having a porosity and an average pore size lying within a range enclosed with lines connecting the X (porosity (%)) and Y (average pore size ($\mu$m)) coordinates of points A (46, 180), B (46, 520), C (50, 520), D (72, 220), and E (72, 180) by mixing granules having a granule size in the range of 0.1 to 2.0 mm, composed of a titanium or a titanium alloy powder having a maximum particle size of 180 $\mu$m or less and an organic binder, with a particulate pore-forming material, pressure-molding the mixture to obtain a molded body, and firing the molded body;

bringing the porous body into contact with an aqueous alkali solution; then bringing the porous body into contact with water until the alkali concentration of the porous body becomes 0.3% or less; and subsequently heating the porous body at 60 to 650° C.

2. The method of claim 1, wherein the pore-forming material is at least one selected from ammonium hydrogen carbonate and oxalic acid.

3. The method of claim 1 or 2, wherein the step of heating is performed in the step of bringing the porous body into contact with water.

4. The method of claim 2, wherein the organic binder is polyacetal.

* * * * *